US008964938B2

(12) United States Patent
Bernhardt et al.

(10) Patent No.: US 8,964,938 B2
(45) Date of Patent: Feb. 24, 2015

(54) METHOD FOR ACQUIRING X-RAY IMAGES

(75) Inventors: Philipp Bernhardt, Forchheim (DE); Martin Spahn, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 242 days.

(21) Appl. No.: 13/493,658

(22) Filed: Jun. 11, 2012

(65) Prior Publication Data
US 2012/0314839 A1 Dec. 13, 2012

(30) Foreign Application Priority Data
Jun. 10, 2011 (DE) .................. 10 2011 077 411

(51) Int. Cl.
*H05G 1/64* (2006.01)
*A61B 6/00* (2006.01)

(52) U.S. Cl.
CPC .............. *A61B 6/405* (2013.01); *A61B 6/482* (2013.01); *A61B 6/4233* (2013.01); *A61B 6/4441* (2013.01); *A61B 6/504* (2013.01); *A61B 6/5235* (2013.01)
USPC ......... 378/98.12; 378/5; 378/98.9; 378/98.11

(58) Field of Classification Search
USPC .................. 378/5, 98.9, 98.11, 98.12
See application file for complete search history.

(56) References Cited

U.S. PATENT DOCUMENTS

| 2004/0213377 A1* | 10/2004 | Endo .................. 378/98.11 |
| 2006/0109951 A1* | 5/2006 | Popescu .................. 378/4 |
| 2008/0044073 A1 | 2/2008 | Bernhardt et al. .......... 382/128 |

FOREIGN PATENT DOCUMENTS

| DE | 10224227 A1 | 12/2003 | ............ G01T 1/20 |
| DE | 102006025423 A1 | 12/2007 | ............ A61B 6/00 |

OTHER PUBLICATIONS

German Office Action, German Patent Application No. 10 2011 077 411.4, 7 pages.
Spahn, M., "Flat Detectors and Their Clinical Applications", Springer-Verlag 2005, Eur Radiol 15, pp. 1934-1947.

* cited by examiner

Primary Examiner — Glen Kao
(74) Attorney, Agent, or Firm — King & Spalding L.L.P.

(57) ABSTRACT

A buffer on detector elements of an X-ray radiation detector can be used, when acquiring a number of 2D X-ray image data records with the aid of an X-ray angiography system, to acquire 2D image data records at a relatively short interval one after the other with the aid of different X-ray spectra, to allow dual-energy imaging, which may be of particularly good quality.

9 Claims, 5 Drawing Sheets

METHOD FOR ACQUIRING X-RAY IMAGES

CROSS-REFERENCE TO RELATED APPLICATIONS

This application claims priority to DE Patent Application No. 10 2011 077 411.4 filed Jun. 10, 2011. The contents of which is incorporated herein by reference in its entirety.

TECHNICAL FIELD

This disclosure relates to a method for acquiring X-ray images, in particular with the aid of an X-ray angiography system, which comprises an X-ray radiation source and an X-ray radiation detector, which together are disposed on a C-arm and are moved into different positions during the recording of different X-ray images, in that the X-ray C-arm is rotated about an axis. The disclosure deals in particular with imaging using different X-ray spectra allowing certain structures to be highlighted. Such so-called dual-energy imaging functions as follows: different chemical materials absorb X-ray radiation at a certain frequency to a differing degree. This is also true of biological tissue. For example bone tissue can absorb X-ray radiation at a first frequency to a greater degree than at a second frequency, while soft tissue can absorb X-ray radiation at the second frequency to a greater degree than at the first frequency. If different energy spectra are then used, which differ in their respective proportions of radiation at the first frequency and at the second frequency, the following can take place: the data values from the one image data record are used and added, in each instance weighted, to the data values of the second image data record corresponding to the same image points. It is possible to highlight different structures in the X-ray images that can be thus acquired, depending on the weights selected.

BACKGROUND

Acquiring fairly large numbers of X-ray images with the aid of an X-ray angiography system requires the individual 2D image data records to be obtained at a high speed, if a 3D image data record is to be calculated from the totality of said 2D image data records (known as reconstruction). This is because the image object, usually a person (patient), naturally always moves as the image is being recorded and the longer it takes to acquire to acquire the X-ray images, the greater the blurring in the image.

The X-ray radiation detectors used in X-ray angiography systems generally have a scintillator, which converts X-ray beam quanta striking the X-ray radiation detector to light quanta. The X-ray radiation detector also has a grid or matrix of detector units, each detector unit having a light-sensitive receiver, at which a measurement value is changed by light quanta striking it. The light-sensitive receiver is typically a photodiode and the measurement value relates to a voltage that increases due to incident light quanta.

The photodiodes are typically read out in a central memory. Reading out can only take place line by line and therefore takes a relatively long time.

If two X-ray image data records are to be acquired, each with the aid of an X-ray angiography system, specifically with different spectra, and a sufficiently large number of 2D X-ray image data records in total are to be acquired in a short time, the problem arises that the photodiodes may be read out too slowly.

From other applications it is known that a buffer can be provided on detector elements, into which buffer the measurement values from the respective light-sensitive receivers can be read out so that the receivers can then be reset to zero. The buffer can be read out at a later time. CMOS technology or a related technology is particularly suitable for implementing such a buffer. CMOS stands for Complementary Metal Oxide Semiconductor.

SUMMARY

In one embodiment, a method is provided for acquiring X-ray images with the aid of an X-ray radiation detector, which has a scintillator, which converts X-ray beam quanta striking the X-ray radiation detector to light quanta and which also has a grid of detector units, each detector unit having a light-sensitive receiver, at which a measurement value is changed by light quanta striking it, and each detector unit having a buffer for measurement values read out from the light-sensitive receiver, wherein with the method: (a) the measurement value at all the light-sensitive receivers is reset to a predefined value, (b) X-ray radiation with a first spectrum is emitted from an X-ray tube, so that said X-ray radiation passes through an image object and then strikes the X-ray radiation detector, (c) the measurement value is read out from all the light-sensitive receivers into the associated buffer and then reset to the predefined value in each receiver, (d) X-ray radiation with a second spectrum is emitted from the X-ray tube, so that said X-ray radiation passes through the image object and then strikes the X-ray radiation detector, (e) the measurement value is read out from all the buffers into a central memory, giving a 2D X-ray image data record for the first spectrum, and (f) the measurement value is read out from all the light-sensitive receivers into the central memory, giving a 2D X-ray image data record for the second spectrum.

In a further embodiment, the measurement value in step (f) is read out by way of the buffer. In a further embodiment, the method is performed repeatedly, in which process the X-ray radiation detector and the X-ray tube are rotated together about an axis, so that between step (b) and step (d) rotation takes place at a first rotation angle and between step (d) and the next repetition of step (b) rotation takes place at a second rotation angle, which is greater than the first rotation angle. In a further embodiment, the new image data record ($g_{new,1}$; $g_{new,2}$) is calculated by means of a weighted addition or subtraction image point by image point of the data values of the first and second image data record.

BRIEF DESCRIPTION OF THE DRAWINGS

Example embodiments will be explained in more detail below with reference to figures, in which.

DETAILED DESCRIPTION

Figure 1:
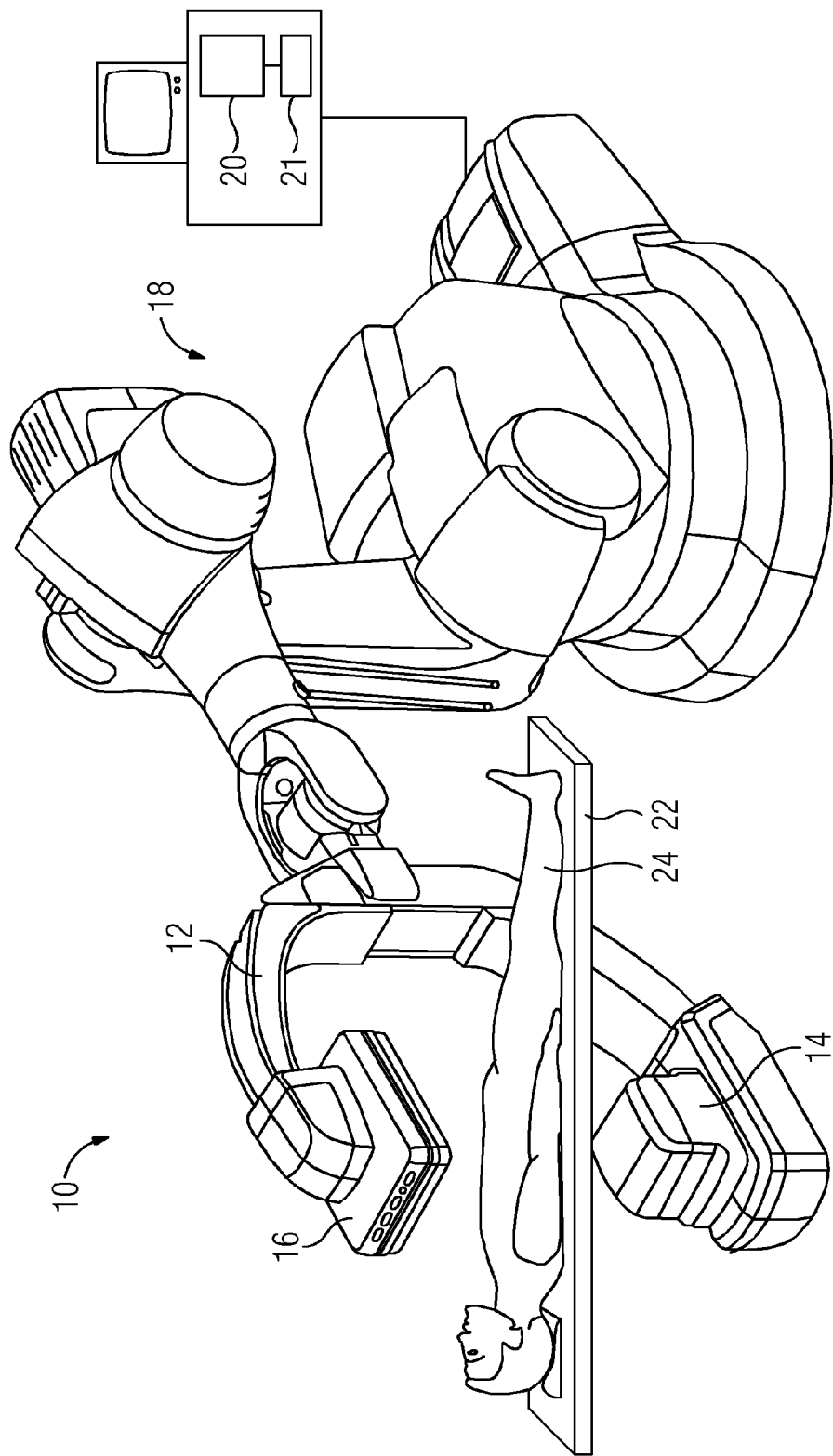
FIG. 1 shows a perspective diagram of an X-ray angiography system, according to certain embodiments.

Some embodiments provide an efficient method for acquiring X-ray images with different spectra, which can be realized for example with an X-ray angiography system, so that the achievable image quality is high or even as high as possible.

X-ray images are thus acquired with the aid of an X-ray radiation detector, which in addition to a scintillator and a grid of detector units with light-sensitive receivers (photodiodes) on each detector unit has a buffer for measurement values read out from the light-sensitive receiver. The method may comprise the following steps:

In step a) the measurement value at all the light-sensitive receivers is first reset, i.e. the voltage is set to a fixed negative value (bias voltage).

In step b) X-ray radiation with a first spectrum is emitted from an X-ray tube, so that it passes through an image object and then strikes the X-ray radiation detector. In this process the photodiode is partially or even fully discharged as a function of the incident light.

In step c) the measurement value is read out from all the light-sensitive receivers and stored in the associated buffer (of the same detector element). The measurement value is again set to negative bias voltage in each light-sensitive receiver.

In step d) X-ray radiation with a second spectrum is emitted from the X-ray tube, so that it passes through the image object and then strikes the X-ray radiation detector.

In step e) the measurement value is read out from all the buffers into a central memory after or at the same time as step d, giving a 2D X-ray image data record for the first spectrum.

In step f) the measurement value is also read out from all the light-sensitive receivers into the central memory, giving a 2D X-ray image data record for the second spectrum.

In this manner a minimum amount of time is lost between the recording of two X-ray images, in other words between the acquisition of two 2D X-ray image data records, with different spectra, because the measurement value does not have to be read out directly from the light-sensitive receivers into the central memory in a time consuming manner but can be read out into the buffer in a time-saving manner.

This allows well matched 2D X-ray image data records to be acquired for different spectra, even if the X-ray radiation detector and the X-ray radiation source are continuously rotating, so that certain structures in the image object can be imaged particularly accurately.

In one embodiment the measurement value in step f) is first read into the buffer or read out from the light-sensitive receiver into the buffer and then read out from the buffer into the central memory. With this embodiment no special read-out mechanism is required from the light-sensitive receiver to the central memory. Instead it is sufficient to have read-out facilities for reading a measurement value out from the respective light-sensitive receiver into the buffer and at the same time to have read-out facilities for reading a measurement value out from the buffer into the central memory. This allows the X-ray radiation detector used for the method to be structured in a compact and uncomplicated manner.

In one embodiment the method is performed repeatedly, in which process or while the X-ray radiation detector and the X-ray tube are rotated together about an axis. Between step b) and step d) rotation takes place at a first rotation angle. Between step d) and the next repetition of step b) rotation takes place at a second rotation angle and the second rotation angle is greater than the first rotation angle. This achieves the effect that the two 2D X-ray image data records acquired in the associated steps e) and f) match one another better than different 2D X-ray image data records from subsequent runs through the method.

It is also possible in this manner to calculate a new image data record by means of a weighted addition or subtraction image point by image point of the data values of the first and second image data record, which is therefore also performed as a matter of preference. If according to the method disclosed herein the X-ray images can be acquired efficiently and the two image data records match particularly well, then the quality of the image data records acquired by weighted addition or subtraction image point by image point may be particularly good. More than one new image data record can be acquired, if the respective weights are selected as different from one another.

An X-ray angiography system designated as a whole as 10 has an X-ray C-arm 12, on which an X-ray radiation source 14 (X-ray tube) and an X-ray radiation detector 16 are disposed. The X-ray C-arm 12 is disposed on a six-axis buckling arm robot 18, which is actuated by a central control unit 20 with a central memory 21. A patient table 22 holding a patient 24 is in such a position that X-ray radiation leaving the X-ray radiation source 14 passes through the body of the patient 24, before it strikes the X-ray radiation detector 16.

Figure 2:
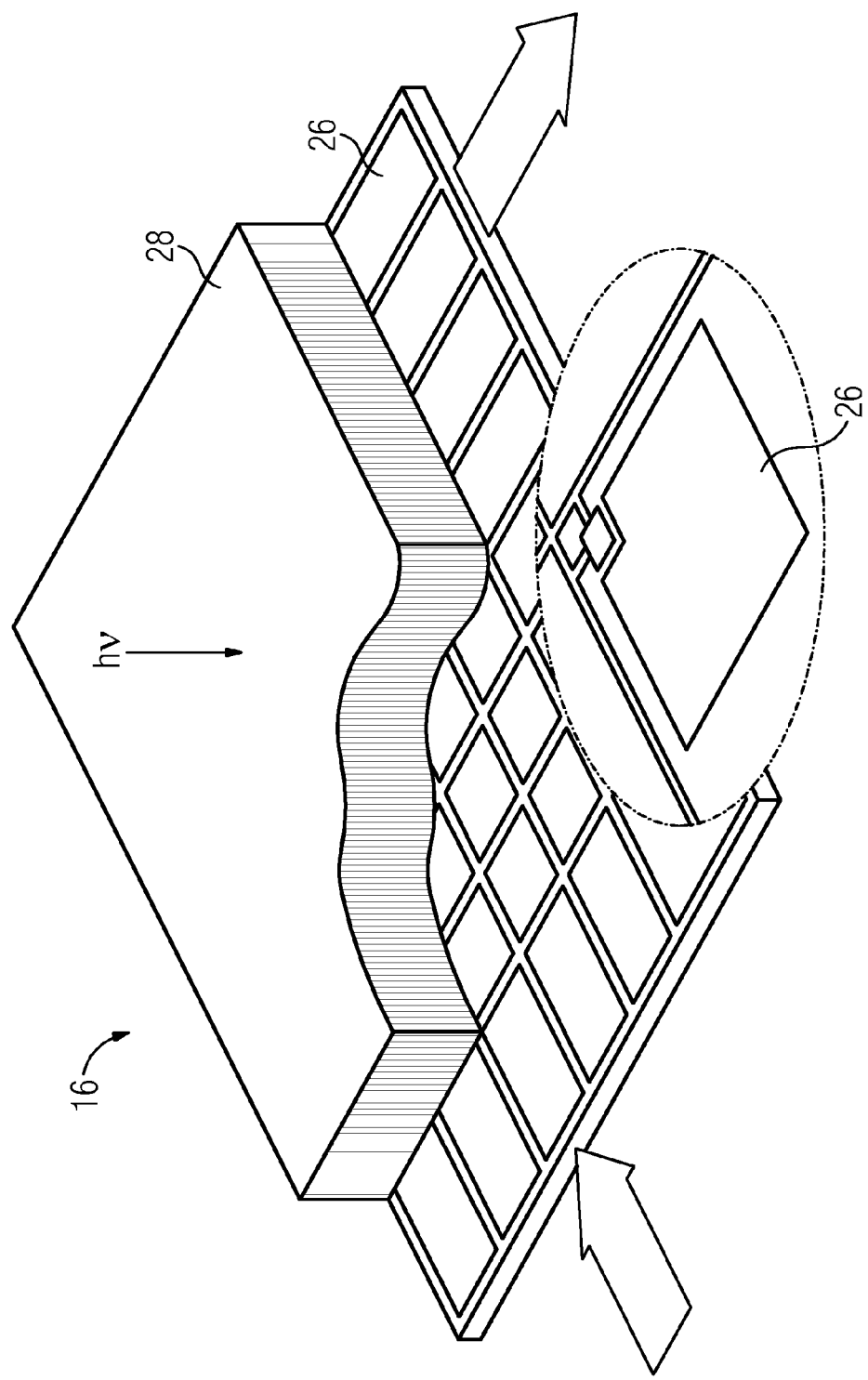
FIG. 2 shows a perspective, partially sectional, diagram of an X-ray radiation detector, according to certain embodiments.

According to FIG. 2 each X-ray radiation detector 16 includes a plurality of X-ray radiation detector elements 26, one of which is shown enlarged in FIG. 2. Present on the detector elements 26 is a layer of scintillator material 28, which converts incident X-ray beam quanta hv to light quanta.

Figure 3:
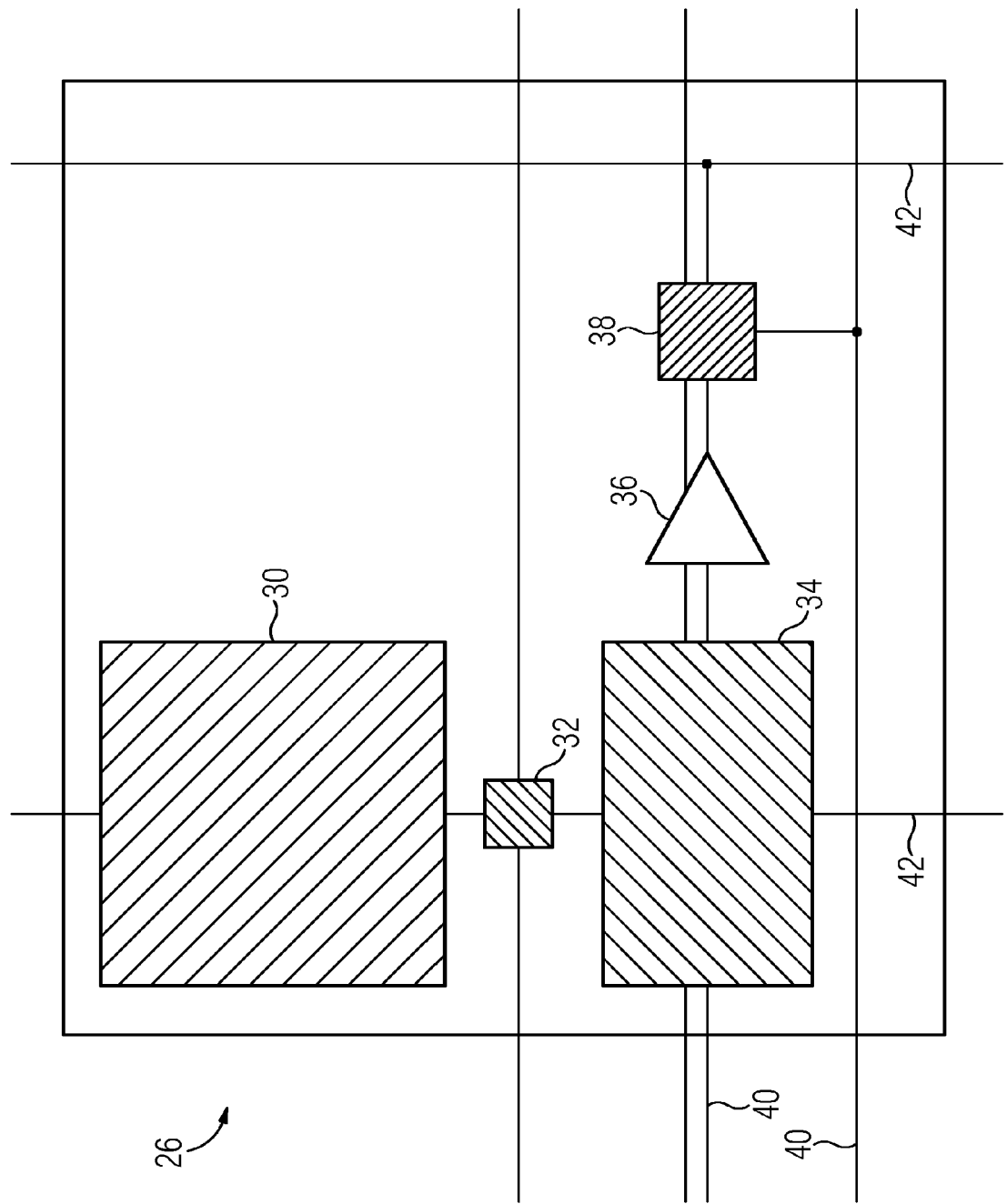
FIG. 3 shows a schematic drawing to illustrate the structure of a detector element of the X-ray radiation detector, according to certain embodiments.

In the present instance the individual detector elements 26 are structured as shown in FIG. 3:

A photodiode 30 converts light quanta, which leave the scintillator 28, to an electrical voltage proportional to the number of light quanta, until the voltage is reset to a negative value (bias voltage). Disposed next to the photodiode 30 is what is known as a transfer gate 32, which has the task of passing on the charge at the photodiode 30, in the present instance specifically to a buffer 34. Downstream of the buffer 34 are an amplifier 36 and a switching transistor 38, so that the data values (in other words the charge measurement values or voltage measurement values corresponding to said charge) can be read out from the buffer into the central memory 21 by way of lines of read-out lines 40 and columns of read-out lines 42. In the present instance the individual detector elements 26 are to be implemented using CMOS technology or related technologies.

The structure of a detector element in the manner of the detector element 26 from FIG. 3 is known in principle. In the present instance interest is focused on a particular application in the X-ray angiography system 10: dual-energy 3D imaging is to take place, in other words imaging in which a 3D image data record, in which gray scale values are assigned to a plurality of volume elements in the three-dimensional space, is calculated from 2D image data records, the dual-energy imaging meaning that the gray scale values allow a representation in which certain body structures are highlighted in particular. For dual-energy imaging two 2D X-ray image data records are recorded in each instance, with a change being made to the X-ray spectrum.

The approach involving switching between two spectra at short time intervals can be implemented using the following methods:

More modern generators and primarily pulsed X-ray tubes can at present change the high voltage between two pulses within a few milliseconds. In the simplest instance, as in standard pulse operation, the high voltage is switched off after the end of the first pulse. After a few milliseconds another high voltage is selected for the next pulse. Such a kV change is possible even without interruption; the generator simply selects a new voltage during a pulse. It is important here that the generator detects the resulting tube current when the high voltage changes and corrects it as quickly as possible if necessary. Different high voltages also have an influence on the electron emission of the coil (by way of the field emission). Therefore higher voltages generally require a smaller coil heat output.

An improvement is also achieved in the distinction between two spectra by changing the prefiltering. In the present instance this is done with the aid of filter elements (not shown in the figures) which can be inserted and removed quickly. Such filter elements can currently be inserted and removed with the aid of mechanical springs within 100 ms. It can be done even more quickly with wedge filters, which can be moved to and fro linearly or by rotation in the beam path, thereby bringing about a fast change in the prefiltering.

If there is a wish to dispense completely with filter changes, it is also possible to generate a different focal spot for the different spectra, as is possible in what are known as double anode tubes or X-ray tubes with two focal paths. It is then possible to select the most expedient prefiltering for each focal spot beforehand. It is important here that the focal spots are not too far apart so that the dual-energy subtraction is still possible.

The procedure according to one alternative is first described with reference to FIG. 5.

In the present instance there is a system trigger, which provides impulses 46 according to the curve 44. The system trigger means that the so-called integration window of the photodiodes 30 is open, see pulse 48. Immediately afterwards, according to the curve 50, X-ray radiation with a spectrum A starts to be emitted. The photodiodes measure the light quanta, with integration of the measurement values taking place in a manner known per se. After termination of the X-ray beam impulse, according to the curve 52, a data transfer impulse 54 takes place from the photodiodes 30 to the respective buffer 34. Then, according to the curve 57 and pulse 58, the photodiodes are reset. Two processes now continue simultaneously: The data values stored in the buffers 34 of all the detector elements 26 are read out into the central memory 21 according to the curve 58. At the same time, according to the curve 48, the photodiode integration window is opened again and X-ray radiation with spectrum B is now emitted according to the curve 60. Once the image has been recorded, some more time is spent reading out according to the curve 58. As soon as the first image for spectrum A has been read out, a data transfer can take place according to the curve 52 from the photodiodes 30 into the respective buffer 34. Once the voltage values have been read from the photodiodes 30 into the corresponding buffer 34, the photodiodes can be reset once again and the second X-ray image can then be read out into the central memory 21, in other words the 2D image data record for spectrum B, see the curve 58 again. A pulse 46 then passes through the system support again and the method is repeated; a second image is recorded for X-ray spectrum A and a second image is recorded for X-ray spectrum B, etc.

Figure 5:
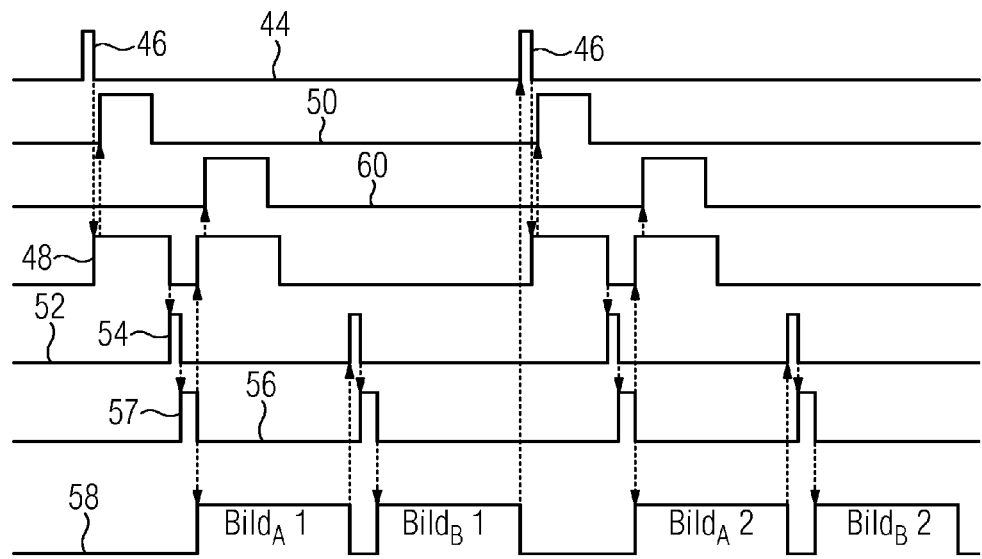
FIG. 5 and FIG. 6 show time curves for different digital variables, corresponding with two embodiments.
Figure 6:
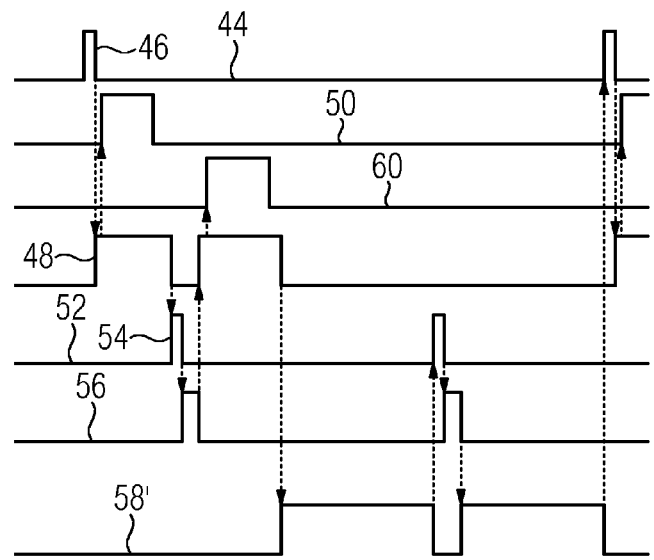

In an alternative procedure according to FIG. 6 the process is essentially the same as with the method according to FIG. 5 but in contrast to what is described there, reading out from the buffers does not take place at the same time as the acquisition of X-ray images for spectrum B but afterwards, see the curve 58' in FIG. 6. This slows the time period down overall. However the method according to FIG. 6 is possibly more efficient in acquiring data with as little interference as possible.

Figure 4:
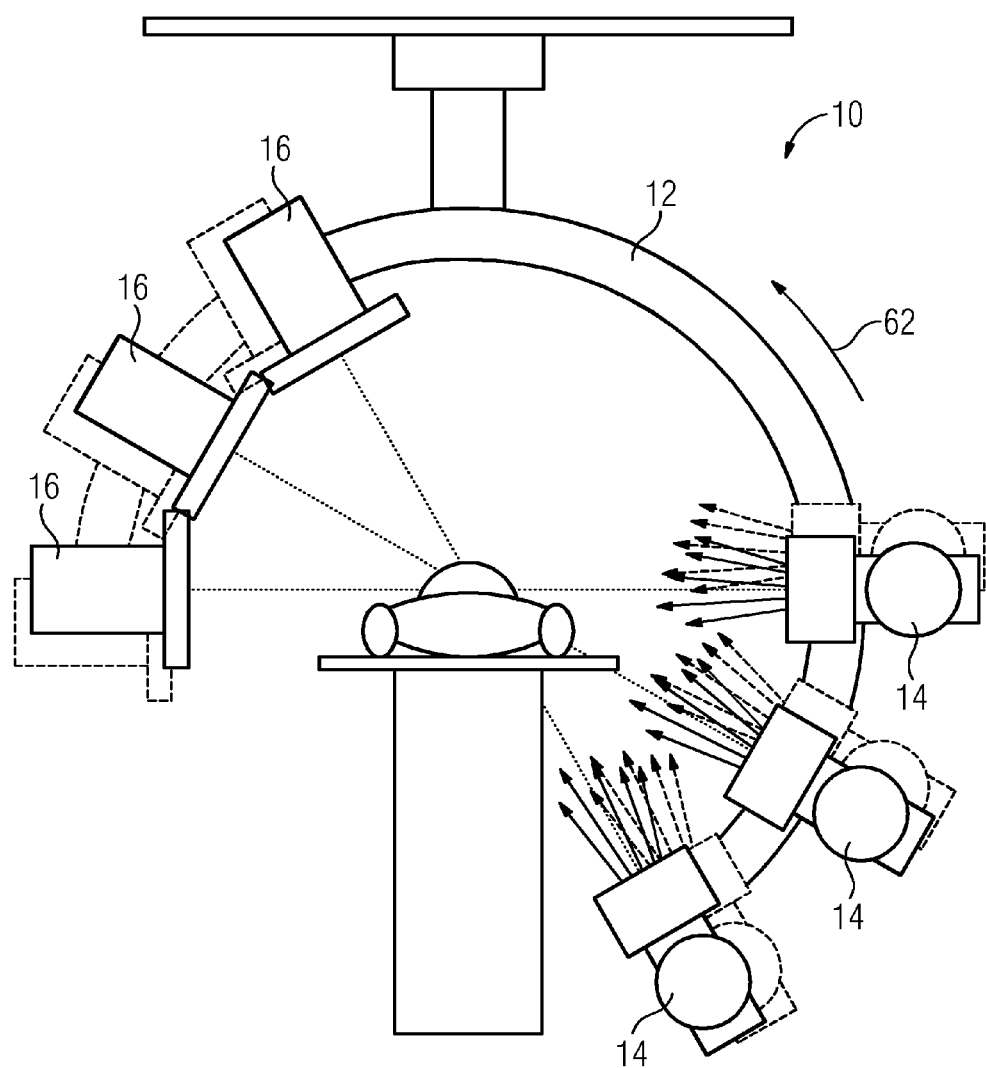
FIG. 4 shows a relative position of X-ray radiation source and X-ray radiation detector in the X-ray angiography system from FIG. 1, according to certain embodiments.

Common to the method according to FIG. 5 and FIG. 6 is the fact that the X-ray radiation source 14, as shown in FIG. 4, experiences a continuous rotation of the X-ray C-arm according to the arrow 62 (FIG. 4) when recording the images with spectrum A on the one hand and only travels a short distance for spectrum B on the other hand, see the difference between the continuous lines in FIG. 4 and the broken lines, whereas it is rotated through a larger angular range between two different imaging passes, see the distance between two representations of the X-ray radiation tube 14 with a continuous line and broken line respectively.

The angular distances here are predefined by the timing according to the curve 48.

For example 300 image pairs are acquired over an angular range of 200°, which is passed through in a regular fashion, in 5 seconds.

X-ray radiation images are now available. If we refer to the gray scale values from a certain 2D X-ray image data record recorded with spectrum A as $g_A$ and the corresponding gray scale values from the 2D image data record recorded with spectrum B as $g_B$, new 2D image data records are calculated using the formula $g_{new,1}=a_1 \cdot g_A + a_2 \cdot g_B$. Bone tissue can then be represented particularly clearly for example in corresponding image representations of the gray scale values $g_{new,1}$. Other weighting factors can be used in a similar fashion, for example: $g_{new,2}=b_1 \cdot g_A + b_2 \cdot g_B$. The gray scale values $g_{new,2}$ can be used for example to represent soft tissue particularly clearly.

Other weightings can be used for example to represent objects that are not part of the body, such as stents, particularly clearly.

A plurality of 2D image data records $g_{new,1}$ or $g_{new,2}$ is thus obtained for different positions of the X-ray radiation source 14 and the X-ray radiation detector 16, thereby allowing a 3D image data record to be reconstructed in each instance. Representations can be produced in any manner from the 3D image data records, e.g. slices, projections or volume renderings. A combined 3D image data record can be calculated instead of two 3D image data records.

What is claimed is:

1. A method for acquiring X-ray images with the aid of an X-ray radiation detector comprising a scintillator that converts X-ray beam quanta striking the X-ray radiation detector to light quanta and also comprising a grid of detector units, each detector unit having a light-sensitive receiver at which a measurement value is changed by light quanta striking the light-sensitive receiver, and each detector unit having a buffer for measurement values read out from the light-sensitive receiver, the method comprising:
(a) resetting the measurement value at each of the light-sensitive receivers to a predefined value,
(b) emitting X-ray radiation with a first spectrum from an X-ray tube, such that said X-ray radiation with the first spectrum passes through an image object and then strikes the X-ray radiation detector,
(c) reading out a first measurement value from each of the light-sensitive receivers into a buffer associated with each respective receiver, each first measurement value corresponding to X-ray radiation with the first spectrum detected by the respective light-sensitive receiver, and then resetting the measurement value to the predefined value in each receiver,
(d) emitting X-ray radiation with a second spectrum from the X-ray tube, such that said X-ray radiation with the second spectrum passes through the image object and then strikes the X-ray radiation detector,
(e) reading out the first measurement values from all of the buffers into a central memory, thereby generating a 2D X-ray image data record for the first spectrum, and
(f) reading out a second measurement value from each of the light-sensitive receivers into the central memory, each second measurement value corresponding to X-ray radiation with the second spectrum detected by the respective light-sensitive receiver, thereby generating a 2D X-ray image data record for the second spectrum, wherein the step of emitting X-ray radiation with the second spectrum from the X-ray tube is initiated during or prior to the step of reading out the first measurement values from the buffers.

2. The method of claim 1, wherein the measurement value in step (f) is read out from the buffer.

3. The method of claim 1, wherein the method is performed repeatedly, and wherein the X-ray radiation detector and the X-ray tube are rotated together about an axis, such that between step (b) and step (d) rotation takes place at a first rotation angle and between step (d) and the next repetition of step (b) rotation takes place at a second rotation angle greater than the first rotation angle.

4. The method of claim 1, wherein a new image data record is calculated using a weighted addition or subtraction image point by image point of the data values of the first and second image data record.

5. The method of claim 1, wherein the step of emitting X-ray radiation with the second spectrum from the X-ray tube is completed prior to initiating the step of reading out the first measurement values from the buffers.

6. The method of claim 1, wherein the step of emitting X-ray radiation with the second spectrum from the X-ray tube is performed at least partially simultaneously with the step of reading out the first measurement values from the buffers.

7. A method for acquiring X-ray images with the aid of an X-ray radiation detector comprising a scintillator that converts X-ray beam quanta striking the X-ray radiation detector to light quanta and also comprising a grid of detector units, each detector unit having a light-sensitive receiver at which a measurement value is changed by light quanta striking the light-sensitive receives, and each detector unit having a buffer for measurement values read out from the light-sensitive receiver, the method comprising:

emitting X-ray radiation with a first spectrum from an X-ray tube, such that said X-ray radiation with the first spectrum passes through an image object and then strikes the X-ray radiation detector, reading out a first measurement value from each of the light-sensitive receivers into a buffer associated with each respective receiver, each first measurement value corresponding to X-ray radiation with the first spectrum detected by the respective light-sensitive receiver, emitting X-ray radiation with a second spectrum from the X-ray tube, such that said X-ray radiation with the second spectrum passes through the image object and then strikes the X-ray radiation detector, reading out a second measurement value from each of the light-sensitive receivers into a buffer associated with each respective receiver, each second measurement value corresponding to X-ray radiation with the second spectrum detected by the respective light-sensitive receiver, reading out the first measurement values from all of the buffers into a central memory, thereby generating a 2D X-ray image data record for the first spectrum, reading out the second measurement values from all of the buffers into a central memory, thereby generating a 2D X-ray image data record for the second spectrum, and wherein the step of emitting X-ray radiation with the second spectrum from the X-ray tube is initiated during or prior to the step of reading out the first measurement values from the buffers.

8. The method of claim 7, wherein the step of emitting X-ray radiation with the second spectrum from the X-ray tube is completed prior to initiating the step of reading out the first measurement values from the buffers.

9. The method of claim 7, wherein the step or emitting X-ray radiation with the second spectrum from the X-ray tube is performed at least partially simultaneously with the step of reading out the first measurement values from the buffers.

* * * * *